(12) United States Patent
Stokes et al.

(10) Patent No.: US 7,303,920 B2
(45) Date of Patent: *Dec. 4, 2007

(54) STAINING REAGENT FOR STAINING HEMATOLOGY SAMPLES IN AN AUTOMATED STAINING APPARATUS

(75) Inventors: Barry O. Stokes, Logan, UT (US); Patti A. Nelson, Paradise, UT (US)

(73) Assignee: Wescor, Inc., Logan, UT (US)

( * ) Notice: Subject to any disclaimer, the term of this patent is extended or adjusted under 35 U.S.C. 154(b) by 333 days.

This patent is subject to a terminal disclaimer.

(21) Appl. No.: 11/061,023

(22) Filed: Feb. 18, 2005

(65) Prior Publication Data

US 2005/0148083 A1  Jul. 7, 2005

Related U.S. Application Data

(62) Division of application No. 10/232,474, filed on Aug. 29, 2002, now Pat. No. 6,858,432.

(51) Int. Cl.
*G01N 1/30* (2006.01)
*G01N 33/48* (2006.01)

(52) U.S. Cl. .............. 436/17; 436/8; 436/18; 436/63; 436/800; 252/408.1; 435/40.5

(58) Field of Classification Search ........... 436/8, 436/17, 18, 43, 45, 46, 63, 800; 252/408.1; 435/40.5, 40.51, 40.52
See application file for complete search history.

(56) References Cited

U.S. PATENT DOCUMENTS

| | | |
|---|---|---|
| 3,870,146 A | 3/1975 | Greenfield et al. |
| 4,004,550 A | 1/1977 | White et al. |
| 4,089,989 A | 5/1978 | White et al. |
| 4,290,769 A | 9/1981 | Liao et al. |
| 4,363,632 A | 12/1982 | Custard et al. |
| 4,382,075 A | 5/1983 | Liao et al. |
| 4,392,864 A | 7/1983 | Helfrich et al. |
| 4,595,524 A | 6/1986 | Yip et al. |
| 4,687,489 A | 8/1987 | Rieke et al. |
| 4,741,898 A | 5/1988 | Mallik et al. |
| 4,816,244 A | 3/1989 | Starkweather |
| 5,009,185 A | 4/1991 | Stokes et al. |
| 5,180,606 A | 1/1993 | Stokes et al. |
| 5,318,795 A | 6/1994 | Stokes et al. |
| 6,344,337 B1 | 2/2002 | Mansfield et al. |
| 6,858,432 B2 * | 2/2005 | Stokes et al. .......... 436/46 |

* cited by examiner

*Primary Examiner*—Maureen M. Wallenhorst
(74) *Attorney, Agent, or Firm*—Thorpe North & Western LLP

(57) ABSTRACT

Automated staining equipment that can mix reagents is used to spray a Romanowsky stain onto slide mounted specimens which are then briefly centrifuged. The centrifugation step removes excess stain leaving only a thin film. Depending on the time of the centrifugation step, most of the organic solvent and part of the water in the stain are evaporated by airflow through the equipment. This greatly accelerates the staining reaction and preserves water soluble structures such as the granules in basophilic leukocytes. For optimal performance, this staining procedure requires a thiazin-eosin stain with about 90% to about 40% organic solvent, such as methanol, and only about 10% to about 60% water. This is a unique staining reagent in Romanowsky staining.

17 Claims, 5 Drawing Sheets

Figure 1:
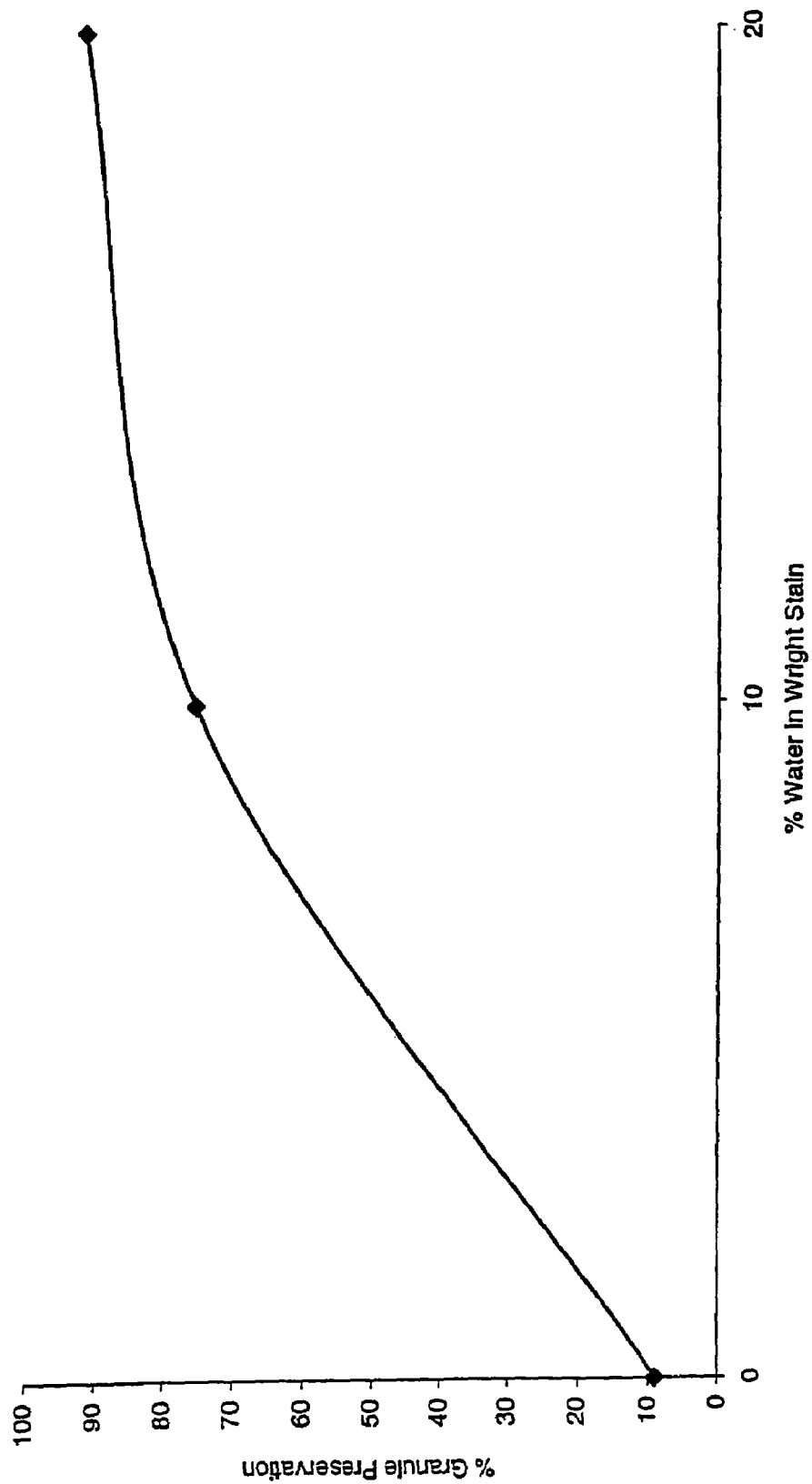

STAINING REAGENT FOR STAINING HEMATOLOGY SAMPLES IN AN AUTOMATED STAINING APPARATUS

RELATED APPLICATIONS

This is a Divisional of application Ser. No. 10/232,474, filed Aug. 29, 2002, and entitled "Method And Staining Reagent For Staining Hematology Samples In An Automated Staining Apparatus," now U.S. Pat. No. 6,858,432.

BACKGROUND OF THE INVENTION

1. Field

The invention is in the field of staining reagents for staining hematology samples using automated staining equipment and in methods used for such staining, particularly in the field generally referred to as Romanowsky staining, which includes variations such as Wright and Giemsa staining.

2. State of the Art

Automated slide staining equipment is currently commercially available. One such stainer is manufactured by Wescor, Inc. of Logan, Utah, and is sold under the name Areospray®. In such stainers, slides to be stained are placed in a slide carousel which is rotated in a spray chamber by a motor. One or more spray nozzles are positioned in the spray chamber adjacent the carousel. During rotation of the carousel, the slides are sprayed with various reagents as they move past the spray nozzles. Pumps are provided to pump reagents from reagent reservoirs to the nozzles which atomize the reagents and spray them onto the slides as the slides pass the nozzles. Such staining equipment is shown, for example, in U.S. Pat. Nos. 5,009,185 and 5,180,606. Automatic staining equipment can be used to perform many types of staining activities, i.e., to carry out various embodiments of various different staining methods, and various different staining reagents are used in performing the many types of staining activities.

Each particular type of staining activity or staining method uses particular reagents such as particular staining and rinsing reagents, and the equipment goes through particular steps to apply the particular reagents in particular orders and amounts while the carousel rotates at particular speeds. The equipment is programmed, either at the factory or by the user, to carry out a particular staining method. The program directs the equipment to draw reagents from particular reagent reservoirs (the user has to place the correct reagents in the correct reservoirs) at particular times and controls both the spraying time and carousel speed to perform the particular method programmed. Usually the equipment is programmed so the user can select between several variations of the method and may be able to select or set one or more of the variables.

In the field of hematology sample staining, there is a type of staining referred to generally as Romanowsky staining. Romanowsky is generally credited with discovery of the unique effects of the thiazin-eosin blood stain in 1891, D. Romanowsky (1891) Zur Frage der Parisitiologie und Therapie der Malaria. St Petersb. med. Wschr. 16, 297-302. and D. Romanowsky (1891) Zur Frage der Parisitiologie und Therapie der Malaria. St Petersb. med. Wschr 16, 307-315. Since that time many variants of Romanowsky staining have been proposed, P. N. Marshall (1978) Romanowsky-type stains in hematology. Histochem. J. 10, 1-29. Popular modem methods are those developed by Wright in the U.S. and Giemsa in Europe. Combination stains such as Wright Giemsa and May-Grünwald Giemsa (Pappenheim) are also widely used. The staining stock solutions for these methods are typically thiazin-eosinates dissolved in organic solvents, principally methanol for Wright and methanol/glycerol for Giemsa. These stains contain no water, but must be diluted with water for final staining to occur. Staining with an alcohol concentration of greater than about 30% slows staining dramatically and completely inhibits the formation of the purple coloration of nuclei (the Romanowsky-Giemsa effect (RGE)). The working stains prepared by diluting the stock solutions are unstable and must be prepared shortly before use. Yip et al., U.S. Pat. No. 4,595,524, avoided stability problems by using separated dye solutions, but mixed them prior to staining as did Romanowsky in the original development of blood staining. The blended Yip stain is primarily aqueous with small amounts of acetone (13%) and dimethyl formamide (6.5%) to reduce precipitation. It is essentially equivalent to a Wright Giemsa stain which has been diluted with buffer for the final staining step.

A rapid methodology is employed in the Wescor Aerospray® 7120 Hematology Stainer which sequentially stains with separate aqueous solutions. Several such stains are available from commercial suppliers. The first stain contains eosin; the second contains thiazin dyes. Keeping the dyes separated avoids stain precipitation and the aqueous solvent allows very rapid staining.

During the course of developing a Romanowsky type staining procedure for the Aerospray® 7120 Hematology Stainer, the absence of basophil granules in the resulting smears was recognized, along with other differences in staining results when compared with the traditional stains. The granules of basophilic leukocytes (basophils) primarily contain histamine and heparin which are small molecules that are highly water soluble. In Wright or Giemsa staining these granules are stabilized by simultaneous binding of thiazin (primarily azure B) and eosin molecules from an aqueous organic solvent suitable for granule preservation. When well stabilized they produce a distinctive appearance. The cell is filled with large blue black granules making identification easy and certain. When the granules are absent, they are easily confused with other cell types unless the observer receives specialized instructions.

In order to stabilize the basophil granules in the Aerospray® 7120, Wescor developed a predip fixative (Basofix®) containing azure B, polyvinylpyrrolidone, methanol, and less than 4% water. Slides are dipped into the solution and then allowed to dry, thereby depositing a film of azure B and PVP on the slide. The basophil granules appear to stain when the eosin stain is applied by the Aerospray® 7120, presumably by producing thiazin-eosinate at the slide surface. Efforts to fix with Basofix inside the instrument produced rather poor results, granules were only half as good as for slides manually fixed outside the instrument. In addition, other cellular granulation such as the primary granulation of immature leukocytes and granulation in segmented neutrophils were not adequately improved whether the fixation was automated or manual. This led to the conclusion that optimal automated staining would require a mixed thiazin-eosin stain for stabilizing the basophils and other granules.

Considerable difficulty was encountered in adapting a Wright/Giemsa application to the Aerospray® 7120. A commercial rapid Wright stain was run on the Aerospray® 7120. In hand staining, this stain is applied to the blood smear in anhydrous form and then the smear is transferred to water to complete the staining reaction. This accomplishes the necessary aqueous dilution. While staining was close to usable in the Aerospray® 7120, after program optimization of alternate stain and water sprays, the basophils were totally degranulated. This was very surprising since the thiazin-eosinate dye combination was expected to stabilize and stain the granules.

FIG. 1 shows that the presence of water is necessary to fix the basophil granules. Slides were placed in a commercial Wright stain, such as made by Harleco, containing varying amounts of water for one minute, then centrifuged in the Aerospray® 7120 for 30 seconds to remove excess stain and dry the slides. The extent of granule preservation was estimated under a 100× oil immersion lense using a light microscope. In the absence of water very little preservation is evident, but granulation increases markedly as the water content is increased.

During hand staining procedures with Wright stain, slides are typically fixed in the anhydrous stain to cause the cells to adhere to the glass slide and stabilize their morphology. This must be done with methanol or anhydrous staining reagent since the presence of water causes cell destruction, cloudiness and water artifacts in the smear. Once fixed, the slides are transferred to a diluted (5 to 100 fold) stain to allow final staining to occur. In such environments, basophil granules dissolve rapidly if not previously stabilized. The above information suggests that in hand staining, the transition from anhydrous stain to aqueous is gradual enough to produce conditions favorable for basophil stabilization. When slides are transferred from the anhydrous stain to a dilute one, the film of stain which is immobilized by the slide is apparently diluted slowly enough to allow the fixation of the basophil granules. In the Aerospray®, the force of the spray droplets impacting the slide appears to penetrate the thin layer of stain held by the vertical slide. This penetration mixes and quickly washes away the dyes thus preventing adequate staining and stabilization of the basophil granules during the rapid transition from anhydrous to diluted stain. During efforts to optimize basophil fixation and staining, a good deal of unpredictable behavior was observed in basophil granulation results. While basophil granules were stabilized, results were nearly always inferior to the simple manual procedure described above. The need remains for a staining procedure or method usable with automatic staining equipment to provide good basophil granulation and good Romanowsky type staining.

SUMMARY OF THE INVENTION

The key to controlling basophil staining has been found to be centrifugal evaporation in conjunction with a special staining reagent having a high concentration of organic solvent. According to the invention, satisfactory Romanowsky type staining (thiazin-eosin staining) of a hematology sample fixed to a microscope slide can be accomplished in automated staining equipment, such as an Aerospray® 7150 stainer which can provide staining reagent mixing at the time of application of the stain and centrifugal evaporation of staining reagents from a sample on a slide, by providing an initial staining step using a thiazin-eosin stain containing only between about 10% to about 60% water and containing between about 90% to about 40% organic solvent, such as methanol. This stain has a much higher organic solvent concentration and much lower water concentration than the prior art stains and than would be expected to work for this type of staining.

Figure 2:
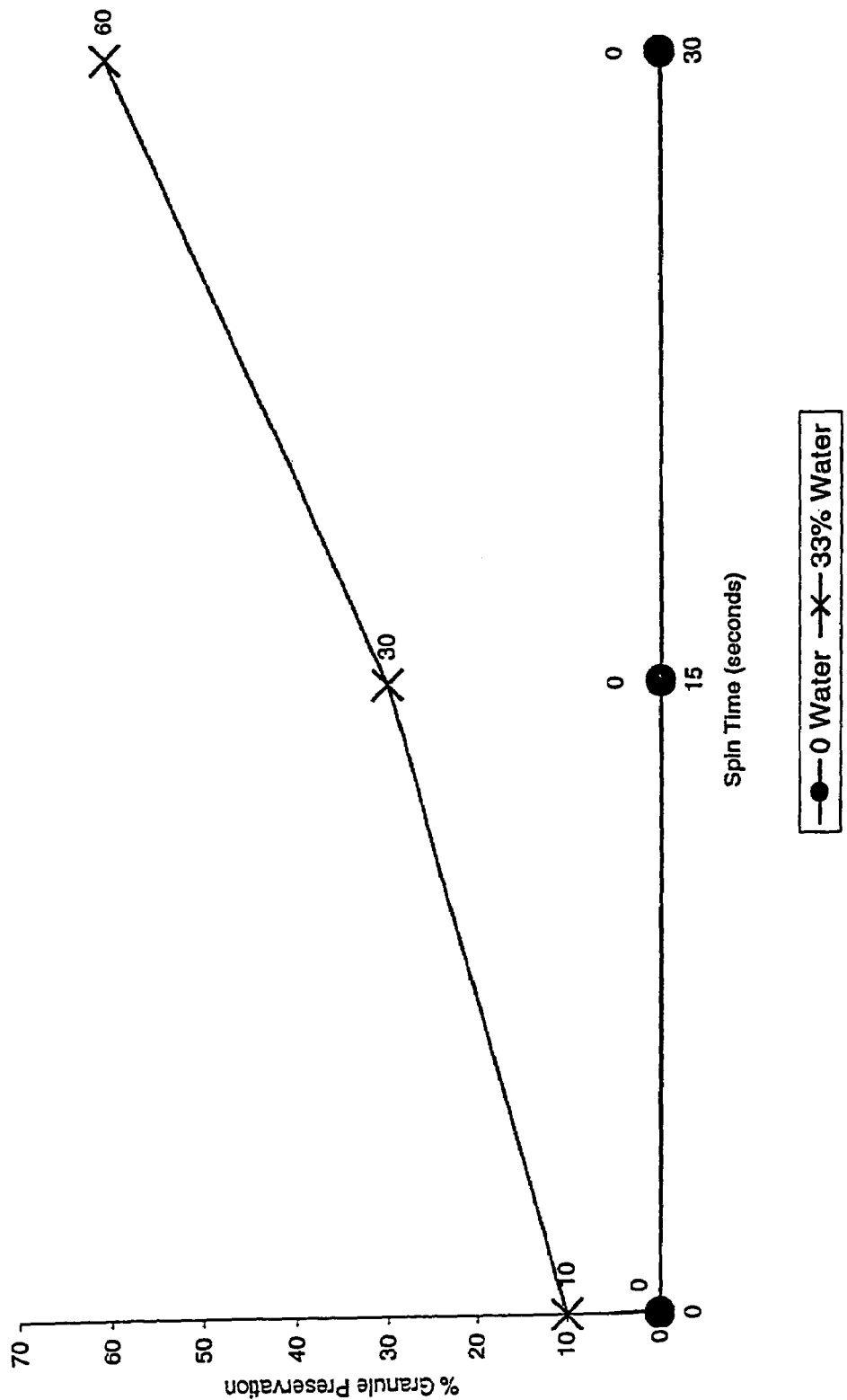

The stain is applied to the slide and sample while the slide is rotating at an application speed in the equipment, usually between about 20 and 30 RPM, to allow the stain applied to the slide to remain on the slide and sample. After application of the stain, the slide is rotated in the staining equipment at a speed, usually at a high speed between about 400 and 2000 RPM, and for a time sufficient to evaporate a portion of the organic solvent and thereby reduce the organic solvent concentration and increase the concentration of stain on the sample. The increased speed spin step was initially tried for the purpose of ending the staining reaction and to dry the slide for examination. The dramatic effect on the stabilization of the basophil granules was quite unexpected. Subsequent experiments showed that when a controlled high speed spin (0 to 30 seconds at 600 RPM) was added to a staining step, basophil granulation improved markedly if water was present in the stain. In one such experiment, after identical applications of concentrated staining solution, slides were subjected to the high speed spin or a combination of the high speed spin and a wait time for a total staining time of thirty seconds. The slides were dried at 900 RPM for thirty seconds and examined and compared. FIG. 2 shows the improved basophil granulation preservation when using a stain having 33% water when applied to the slide versus no water, and shows the improvement in preservation with spin time. This improved basophil granulation preservation may be due to removal of most of the liquid into which the granule material dissolves, thus causing saturation of the small volume of remaining fluid with only minor granule dissolution. A desirable side effect is that the rate of staining of other components is also accelerated.

Figure 3:
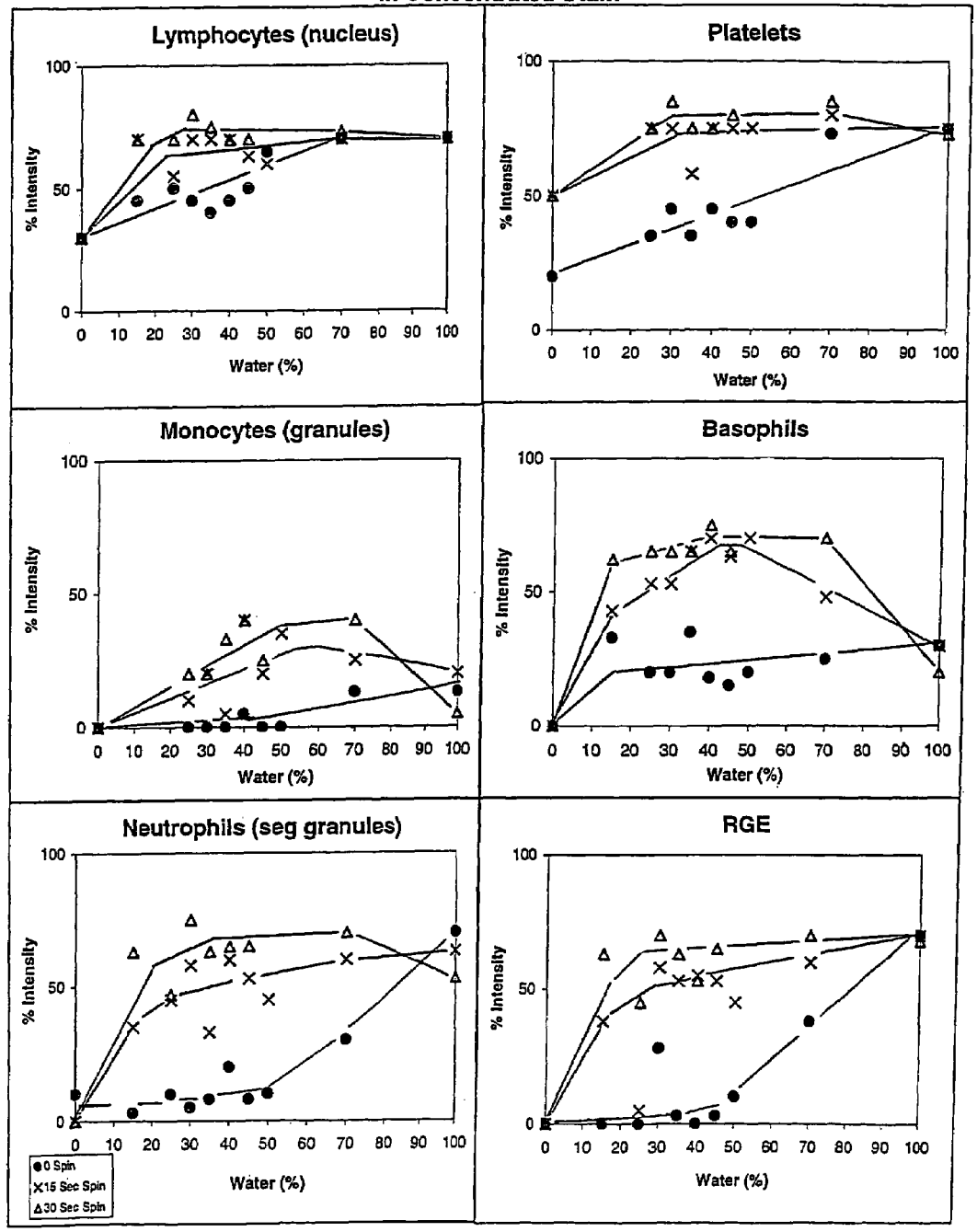

The Aerospray® is constructed to allow air flow through the instrument during high speed centrifugation. We theorize that the principal acceleration of staining is due to evaporation of the methanol from the stain. This improves the dyes' affinity for the cellular substrates and at the same time increases the concentration of stain at the slide surface which further enhances the staining rate. These effects are readily observed by placing a drop of anhydrous Wright stain with 30% water added onto a microscope slide and placing a coverslip over it. Under the coverslip, staining is slow and weak, but at the edges of the coverslip, where evaporation occurs, staining is rapid and intense. The same effect is achieved by the high speed spin of the slides in the Aerospray®. During the high speed spin step, excess stain is thrown from the slide and the methanol evaporates from the residual stain film. This results in an increased staining rate in the basophil granules and many other cellular components. FIG. 3 shows staining intensity versus water concentration for various cellular components and for different evaporation spin times. The cellular components looked at were lymphocytes, platelets, monocytes, basophils, and neutrophils. The RGE (Romanowsky Giemsa Effect) which evaluates the reddish purple color of the cell nuclei was also evaluated and results shown. The spin times compared were zero spin, fifteen second spin, and thirty second spin. Without the centrifugal evaporation or spin step, staining in the Aerospray® would take two to three times as long and consume a great deal more stain. The primary effect is acceleration of thiazin staining. Eosin staining of erythrocytes and eosinophil granules appears to be less affected by centrifugation.

THE DRAWINGS

Figure 4:
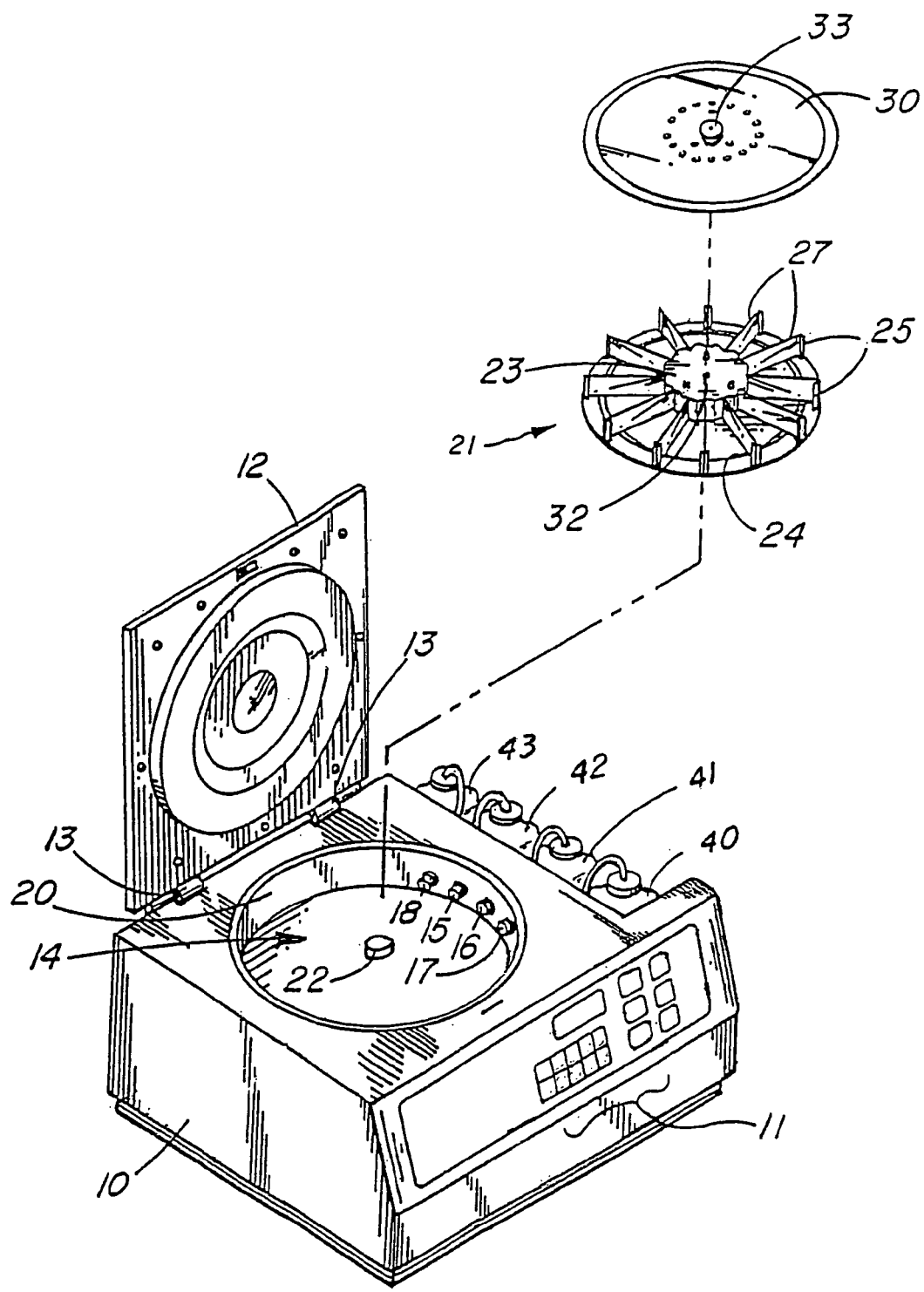
Figure 5:
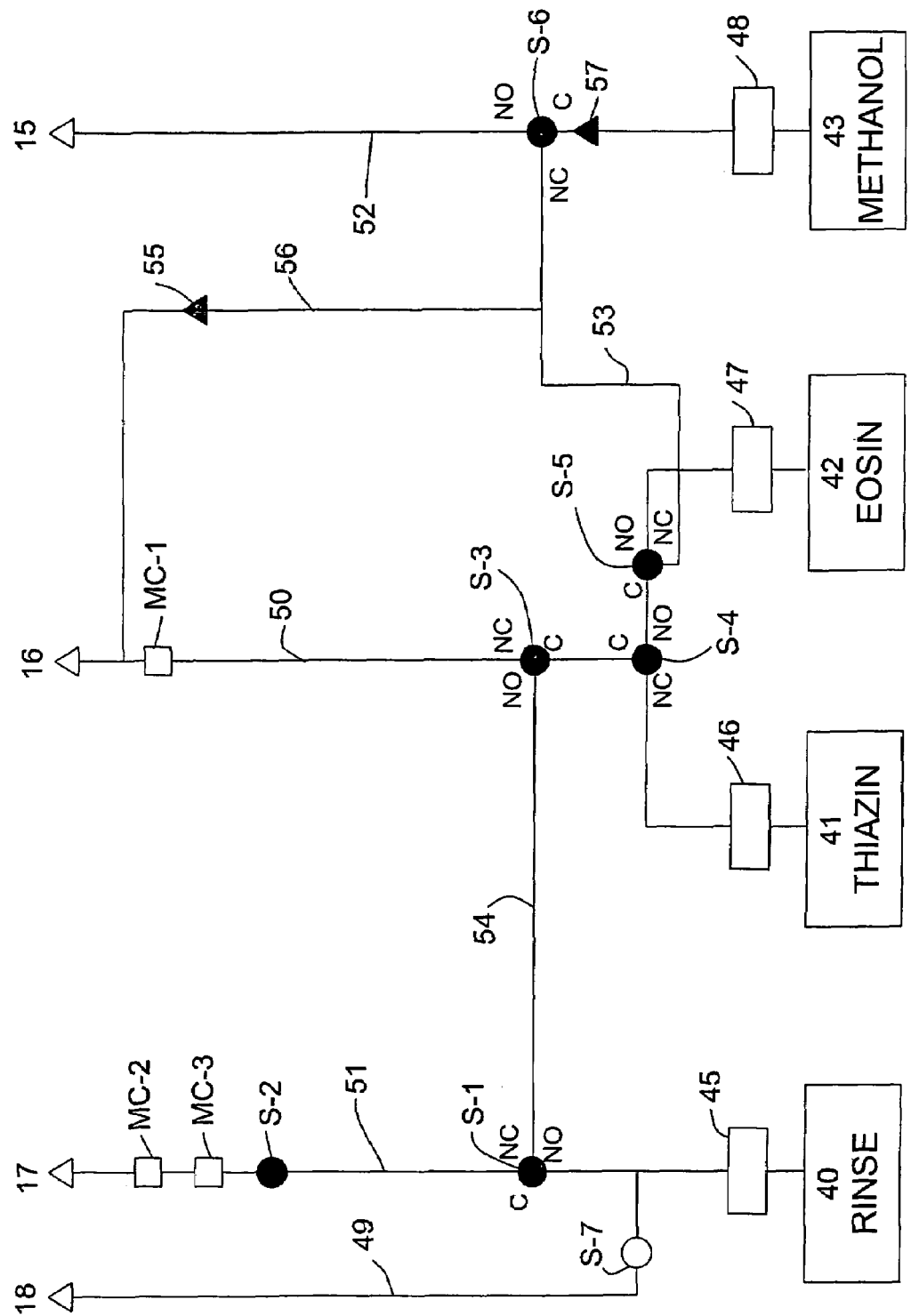

In the accompanying drawings, which show the best mode currently contemplated for carrying out the invention:

FIG. 1 is a graphical representation of the effect of water on basophil staining;

FIG. 2, a graphical representation of the effect of spin time and water concentration on basophil granule preservation;

FIG. 3, a graphical representation of the effect of water and spin time on staining results;

FIG. 4, a perspective view of an embodiment of automatic staining equipment usable for practicing the invention; and FIG. 5, a diagram showing the arrangement of the valves and spray nozzles in an automated stainer used to carry out the process of the invention.

DETAILED DESCRIPTION OF THE ILLUSTRATED EMBODIMENT

The invention is a novel staining process whereby a blood film or other suitable sample is stained for microscopic evaluation using a novel thiazin-eosin stain containing only about 10% to about 60% water. The staining is carried out using automated staining equipment such as shown in U.S. Pat. Nos. 5,009,185 and 5,180,660, incorporated herein by reference, with such equipment providing centrifugal evaporation during certain steps of the staining process. The equipment of the cited patents is commercially available from Wescor, Inc. of Logan, Utah, under the trademark Aerospray®. Equipment designed specifically for carrying out the method of the invention will be available as the Aerospray® 7150 Hematology Stainer.

FIG. 4 shows an embodiment of automated staining equipment as described in the referenced patents and as usable for practice of the current invention. An outer housing 10 encloses the operating components of the equipment and has a control panel 11 thereon easily accessible to a user of the equipment. A top cover 12 is hingedly mounted on top of housing 10 as at 13 and opens to expose a spray chamber 14. Spray nozzles 15, 16, 17, and 18 are arranged about a portion of the outside wall 20 of spray chamber 14. A carousel 21 is adapted to fit into spray chamber 14 over a receiving hub 22 and is adapted for rotation in the spray chamber. Hub 22 is secured to a shaft extending from a motor so that operation of the motor causes rotation of the hub 22 and the carousel 21 mounted thereon. Carousel 21 has a central hub portion 23, a bottom portion 24 extending outwardly from the hub 23, and upstanding slide end holders 25 extending from bottom portion 24 and preferably spaced evenly about the circumference thereof. Hub 23 and slide end holders 25 have slots therein to receive the ends of microscope slides 27 which can be placed to extend between the hub 23 and a slide end holder 25. A carousel cover 30 fits over the top of the carousel 21 and is held in place by a bayonet latching mechanism which engages with a receiving hole 32 in carousel hub 23 and has an enlarged head 33 which allows the engaging mechanism to be easily secured to or removed from the hub and serves as a handle for holding and loading the carousel into spray chamber 14.

In operation of the equipment, the motor is operated to rotate the carousel at a known rate of rotation and reagent to be applied to the slides in the carousel is sprayed through one or more of the nozzles into the spray chamber. Pumps located in housing 10 pressurize and pump reagent from reagent reservoirs 40, 41, 42, and 43 through tubing and control valves to nozzles 15-18. The control valves control duration of spray and, when necessary, mixing of reagents. As the carousel rotates, with each rotation of the carousel, each of the slides pass by the nozzles and reagent sprayed from a nozzle is applied to the slides as they pass by. By controlling the speed at which the carousel rotates and timing the spray of reagent from the nozzles, a desired amount of reagent can be applied to the slides. While four nozzles are shown and only four nozzles are needed for the particular method of this invention, any number of nozzles may be included in the equipment with only those nozzles needed to practice the invention being used. Further, while several nozzles could be used simultaneously to spray a reagent onto a slide rotating in the carousel past the nozzles, generally, for applying a staining reagent to a slide, the reagent will be sprayed from a single nozzle as the slide rotates past the nozzle. In such instance, the slide is sprayed once with the reagent during application of the reagent for each rotation of the carousel. The timing of the spray in conjunction with the speed of rotation of the carousel will determine how many times the slide is sprayed (hit) and thus, the amount of reagent applied to the slide and sample thereon. It is sometimes desirable to spray from two nozzles simultaneously such as where a slide backwash nozzle and slide front wash nozzle are run together so that the slide gets two hits, front and back, during one revolution.

Generally, the speed of rotation of the carousel will be controlled so that a reagent applied to the slide will remain on the slide and sample. Such a speed will be referred to as an application speed. For the equipment shown, application of reagent will be made with the carousel rotating at a speed of between about twenty to about thirty RPM. At these speeds, reagent applied to the slide will generally remain on the slide and sample and will not be thrown off by centrifugal force. Further, the carousel is rotating fast enough so that all slides will be sprayed with a reasonable amount of reagent in a reasonable time. For example, at twenty RPM, reagent will be applied to all slides during a three second spray time. With a six second spray time, all slides will be sprayed twice. At Thirty RPM, all slides are sprayed once in two seconds of spray and twice in four seconds of spray. The number of consecutive times a slide is sprayed during rotation of the carousel may be referred to as the number of hits with a reagent. Thus, a slide will receive two hits of reagent when reagent is sprayed for six seconds and the carousel rotates at twenty RPM. In the equipment, carousel rotation speed and spray time is accurately controlled so that precise and repeatable reagent application is obtained. The equipment shown is constructed with vents in the equipment to allow air flow through the equipment. Generally a vent hole is provided through the top of the equipment at the center of the spray chamber, with one or more additional vent holes along the outside of the spray chamber. The carousel with slides therein acts similarly to a pump rotor to pump air through the equipment from the center of the carousel across the faces of the slides which act as vanes. This air flow will cause evaporation and drying of a reagent applied to a slide. Some air flow may be present at the application speeds, but the air flow will increase significantly at higher speeds. A high speed spin using speeds of rotation between about four hundred and about two thousand RPM will be accompanied with significant air flow and with significant centrifugal force to cause reagent to run off the slide. Wait time is merely time during a slow speed (application speed) rotation when reagent is not being applied.

The basic method of the invention involves applying what will be referred to as a concentrated thiazin-eosin stain to a fixed blood film or sample on a microscope slide and then accelerating the staining by rotating the carousel with the slide therein so as to increase evaporation of components of the concentrated stain, and then rinsing the sample to remove remaining stain and debris. The stain is referred to as a concentrated thiazin-eosin stain because it contains between about 90% to about 40% organic solvent and only about 10% to about 60% water. The stain includes between about 1 and about 5 grams per liter of thiazin-eosin dyes. This basic procedure roughly corresponds to a rapid Wright or rapid Wright-Giemsa procedure. The basic method provides good thiazin-eosin staining (Romanowsky type staining) of the blood samples, with good basophil granule preservation which is expected for this type of staining. However, while good results are achieved with the basic method described, additional staining steps using a dilute staining solution can be added. When using the dilute staining solution, the concentrated staining solution step is used first, at least to the extent necessary to preserve the basophils. In some instances, the concentrated staining step may be used principally to preserve the basophils with actual staining of the sample done principally by the diluted staining solution. Such a procedure using a dilute staining solution roughly corresponds to typical Wright or Wright-Giemsa staining. The particular variations used will depend upon the user's preferences.

The starting point for the method of the invention is a blood film or sample fixed to a microscope slide. Fixing of the sample causes the cells in the sample to adhere to the glass slide and stabilizes their morphology. This fixing can be accomplished in any manner suitable to the specimen either manually outside the staining equipment or by using the staining equipment. The fixing must be done using methanol or anhydrous staining reagent since presence of water causes cell destruction, cloudiness, and water artifacts in the sample. A blood sample can be fixed manually by dipping the slide with sample thereon into anhydrous methanol or by dipping the slide with sample thereon into an anhydrous staining reagent. Fixing can also be done using the automated equipment. In such instance, a slide with sample thereon is placed in the carousel and the slide is sprayed with anhydrous methanol one or more times and allowed to dry as the carousel rotates slowly (20 to 30 RPM). The drying at this slow speed can be considered a wait time. This provides the slide with sample fixed thereto, which is the starting point for the method of the invention.

With the slide with sample fixed thereto in the carousel of the staining equipment, a preferred embodiment of the method proceeds as follows:

Step 1: Applying a Concentrated Staining Solution

Each slide is given one to four hits of a concentrated staining solution as the slide carousel rotates at twenty to thirty RPM. The concentrated staining solution has an organic solvent concentration (the organic solvent is typically methanol) of between about 40% to about 90%, a water concentration of between about 10% to about 60%, and a mixture of eosin and thiazin dyes at a concentration of about 1.0 to about 5.0 g/l. The solution is buffered to a pH of from about 6 to about 9. The solution may also include up to about 10 µl of a surfactant and may also include other solvents and solutes as desired.

Step 2: Controlled Spinning (Centrifugal Evaporation)

A high speed spin, 1 to 60 seconds, is applied to the slides. This is typically done at 400 to 1,000 RPM, but could be done at any speed depending on the desired effect. This step decreases the organic solvent concentration of the residual staining solution layer on the sample and concentrates the staining solution to speed the development of the staining reaction. Concentrating of the staining solution takes place generally because the solvent in the staining solution will evaporate in the increased air flow. A wait time, can be included before moving to the next step. The wait time allows time for staining to take place after the concentration of the staining solution has occurred.

Step 3: Repeat Steps 1 and 2

Repetition of Steps 1 and 2 increases cellular staining and can be done as many times as desired, typically 1 to 3 cycles is adequate due to the rapid staining rate achieved with the concentrated staining solution and high speed spin.

The above steps stabilize the basophil granules and can provide excellent cellular staining when combined with a final rinse (Step 6 described below) to complete the staining and remove stain debris. As indicated, the staining results obtained with this basic method correspond roughly to conventional staining using a rapid Wright or rapid Wright-Giemsa stain. If it is desired to obtain results more like conventional staining using a typical Wright or Wright-Giemsa stain, additional staining steps with a dilute staining solution (1:2 to 1:15 dilution with rinse buffer) may be added, and an optional rinse may be performed prior to the application of the dilute staining solution. The dilute staining solution can be applied in any combination of sprays, spins, and waits desired. Generally, if the typical Wright or Wright-Giemsa results are desired, the concentrated staining steps will be used only to the extent necessary to preserve or stabilize the basophils. However, both full concentrated staining and dilute staining may be used together, as desired. Satisfactory additional rinse and dilute staining steps are as follows:

Step 4: Rinse (Optional)

The slides may be rinsed prior to a dilute staining step, if desired. This is typically three hits (nine seconds spray at 20 RPM) with a dilute buffer and one second spin (400 to 1,000 RPM).

Step 5: Staining with a Diluted Staining Solution (Optional)

The dilute staining solution may be a 1:2 to 1:15 dilution of the concentrated staining solution with rinse buffer. The dilute staining solution can be applied in any combination of sprays, spins, and waits desired, with or without the optional rinse. Typically a cycle will consist of:

a. 1 to 3 hits of diluted staining solution.
   b. 1 to 60 seconds of high speed spin.
   c. 0 to 120 seconds of wait time.
   d. Repetition of above steps as many times as desired.

While the high speed spin also accelerates staining with the diluted stain by providing similar centrifugal evaporation of the organic solvent and concentration of the stain on the sample as with the concentrated stain, the dilution makes the process inherently slower than with the concentrated stain. Typically two to six cycles will be adequate, depending on the stock stain concentration, stain dilution ratio, spin speed, and staining time employed. The wait time allows increased staining by the fluid layer which has been concentrated onto the microscope slide by the centrifugal evaporation. While it is possible to stain with only the dilute staining step in automated staining equipment, it has been found that basophil granules are not adequately preserved without at least one application of the concentrated staining solution as described above. As indicated, satisfactory staining can be accomplished using only the concentrated staining solution. Results will differ slightly between the two approaches.

Step 6: Final Rinse

A final rinse at the end of the staining steps is required to remove excess stain and precipitate formed during staining. It may also contribute to color development depending on the conditions employed. The rinse solution can be virtually any desired rinse solution. It is typically a weakly buffered aqueous solution, but may also contain alcohols or other solvents and surfactants to remove precipitate. It may also employ dyes to apply a final tint to the cells. It is typically applied as three hits (nine seconds of spray at 20 RPM) followed by one second of high speed spin (400 to 1,000 RPM). Waits may also be applied either before or after the high speed spin to vary staining effects.

After the final rinse step, staining is complete and the slide is removed from the equipment for examination and evaluation of the stained sample.

Equipment

Combination thiazin-eosin stains are unstable in any solution with water so cannot be prepared and stored before use. They have to be prepared shortly before use. Water containing thiazin and eosin stains alone are stable and can be prepared ahead and then mixed just prior to use. Thus, the equipment used to carry out the method of the invention has to be able to mix stains to create the staining solution actually applied to the slides.

Automated staining equipment capable of carrying out the method of the invention is as shown in FIG. 4 with tubing, pumps, mixing chambers, and valves arranged as shown schematically in FIG. 5. The tubing, pumps, mixing chambers, and valves of FIG. 5 are all located within the housing 10 of FIG. 4 and connect to the reagent reservoirs 40-43. As shown in FIG. 5, rinse buffer is loaded into reservoir 40, thiazin stain is loaded into reservoir 41, eosin stain is loaded into reservoir 42, and methanol is loaded into reservoir 43. Pumps 45, 46, 47, and 48 pump the buffer, thiazin stain, eosin stain, and methanol from reservoirs 40, 41, 42, and 43, respectively, into the equipment tubing to the various valves, mixing chambers, and nozzles.

As illustrated, the equipment has four nozzles. Nozzle 15 sprays methanol for sample fixation. Nozzle 16 sprays the concentrated staining solution, generally a mixture of thiazin and eosin stains. Nozzle 17 sprays the diluted staining solution, a mixture of concentrated thiazin and eosin stains diluted with rinse buffer solution, or just rinse buffer solution for rinsing. Nozzle 18 sprays both the back and the front sides of the slides with rinse buffer solution. The back side wash nozzle, nozzle 18, is shimmed 12° with respect to the spray chamber wall to point the nozzle directly toward the hub. In this configuration it sprays both the front and the back of the slide. The methanol nozzle, nozzle 15, is placed in the next position with an 8° shim. Nozzles 16 and 17 are placed in the next two positions without shimming.

A 0.8 milliliter mixing chamber MC-1 is used in the concentrated stain line 50 going to nozzle 16 to mix the concentrated thiazin and concentrated eosin stains to form the concentrated staining solution applied to the slide through nozzle 16. This chamber mixes the concentrated thiazin stain and concentrated eosin stain metered by solenoid valve S-4. Solenoid valve S-4 is programmed to operate on a 250 millisecond cycle (alternates between its "off" state with the normally open side open and normally closed side closed and "on" state with the normally open side closed and normally closed side open) when blending the concentrated thiazin and eosin stains for the concentrated staining step. For the embodiment being described, the flow rate of stain through the concentrated staining solution line 50 and out through nozzle 16 is about 0.5 milliliter per second. At this flow rate, the 0.8 milliliter mixing chamber MC-1 contains, at any given time, the output of about 6.4 cycles of operation of solenoid valve S-4. The relative times that solenoid valve S-4 is "off" and "on" during a cycle determines the ratio of eosin stain to thiazin stain in the concentrated staining solution. For example, if solenoid valve S-4 is "off" and "on" for equal times (125 milliseconds each), a 50%-50% mixture is produced. If solenoid valve S-4 is "off" for 187.5 milliseconds and "on" for 62.5 milliseconds, a 75% eosin and 25% thiazin mixture is produced. By controlling the respective "off" and "on" times of solenoid valve S-4, any desired mixture of eosin and thiazin stains can be produced.

Mixing chambers MC-2 and MC-3, both identical to MC-1, are located in the dilute stain and rinse line 51 which connects to spray nozzle 17. The cycle time for solenoid valve S-1 which combines the stain and rinse buffer solutions is 500 milliseconds. At 0.5 milliliter per second flow rate, each mixing chamber contains 3.2 cycles of output. Two smaller mixing chambers instead of one larger mixing chamber is preferably used since the flow velocity is expected to be better in smaller chambers than in a larger chamber. The ratio of thiazin to eosin stain is determined by operation of solenoid valve S-4 and the ratio of concentrated staining solution to rinse buffer solution is determined in similar manner by solenoid valve S-1.

Check valve 55 allows flow of methanol through line 56 and nozzle 16 when solenoid valve S-5 is in rest condition and S-6 is activated, and check valve 57 prevents backflow of methanol to pump 48 and reservoir 43 when pump 48 is not operating.

The operation of the pumps and solenoid valves in the equipment in coordination with rotation of the carousel is controlled by a microprocessor which is programmed to provide a desired sequence of operation of the equipment to carry out the method of the invention. The generally used programmable steps are as follows:

Fixation

Where fixation of the sample on the slides is done in the equipment, operation of pump 48 with solenoid valve S-6 in resting position passes methanol from reservoir 43 through its normally open side into line 52 to nozzle 15. The methanol sprays from nozzle 15 onto any slides rotating in the carousel past nozzle 15 during the time that pump 48 operates and solenoid valve S-6 is in its rest condition.

Setting the Thiazin-Eosin Ratio in Concentrated Stain Step

With pump 46 operating to pump thiazin stain from reservoir 41 to solenoid valve S-4 and pump 47 operating to pump eosin stain from reservoir 42 through the normally open side of resting solenoid valve S-5 to solenoid valve S-4, operation of solenoid valve S-4 will control flow and mixing of the thiazin and eosin stains. Solenoid valve S-4 may be set to actuate on a 250 millisecond cycle as described above to blend the eosin stain and the thiazin stain in a desired ratio. Solenoid valves S-3, S-1, and S-5 act as control valves in resting position to block all flow of stain. Actuating solenoid valve S-3 allows flow of the alternating thiazin and eosin stains as controlled by solenoid valve S-4 through the normally closed side of solenoid valve S-3 to mixing chamber MC-1 and nozzle 16. The alternating thiazin and eosin stains mix as they flow through the lines and mixing chamber MC-1 so are a substantially homogeneously mixed concentrated staining solution when sprayed from nozzle 16 onto any slides rotating in the carousel past nozzle 16.

Diluted Stain Step

The ratio of thiazin stain to eosin stain is set by solenoid valve S-4 as described, but on a variable time cycle in order to keep the operating cycle of solenoid valve S-1 at 0.5 seconds. With solenoid valve S-3 in resting position, the alternating thiazin and eosin stains from solenoid valve S-4 pass through the normally open side of solenoid valve S-3 to line 54 and to solenoid valve S-1 which proportions the stain with the rinse buffer solution pumped from reservoir 40 by pump 45. Solenoid valve S-1 operates on a cycle, such as a 500 millisecond cycle, and in the manner as described for solenoid valve S-4, to alternately allow flow of buffer and stain in set amounts through solenoid valve S-1. The alternating buffer and stain flow through solenoid valve S-2, when actuated, through mixing chambers MC-2 and MC-3 to ensure mixing of the buffer and stain into a substantially homogeneous dilute staining solution, and then to nozzle 17. The dilute staining solution then sprays from nozzle 17 onto any slides rotating in the carousel past nozzle 17. Solenoid valve S-2 is used for stopping and starting flow to spray nozzle 17. The relative cycle times of S-1 and S-4 have to be chosen to ensure that the desired mix of thiazin and eosin stains provided by solenoid valve S-4 flow through solenoid valve S-1. It should be noted that there will be a three to six second lag to clear the line of its previous contents prior to spraying the programmed solution. This will be accomplished in the first nine seconds of application. The length of tubing between solenoid valves S-4 and S-3 should be kept as short as possible (there is about 0.075 milliliter of solution per inch of tubing when one-sixteenth inch inside diameter tubing is used) to minimize the error when different thiazin-eosin ratios are used in the concentrated and diluted stain steps.

Rinse Step

Operation of pump 45 with solenoid valve S-1 in its rest condition allows the rinse buffer solution from reservoir 40 to be pumped through solenoid valve S-1 to solenoid valve S-2 which is operated to control flow of rinse buffer to nozzle 17. Solenoid valve S-7 controls flow of rinse buffer through line 49 to back side wash nozzle 18.

Equipment Clean Cycle

When the equipment is not going to be used for a period of time, such as overnight, the clean cycle can be run to clean staining solution from the equipment. For the clean cycle, solenoid valve S-6 is activated along with pump 48 to pass methanol into line 53 and stop flow to nozzle 15. Solenoid valve S-5 is activated to allow the methanol to flow through valve S-5 and through normally open solenoid valve S-4 in its rest condition to solenoid valve S-3. Solenoid valve S-3 is activated to flush line 50 leading to nozzle 16 and to flush mixing chamber MC-1. To flush line 54 leading to solenoid valve S-1, S-3 is deactivated and S-1 and S-2 are activated. Methanol flows through valves S-1 and S-2, mixing chambers MC-2 and MC-3, and nozzle 17. A short, such as 10 second, high speed spin of the carousel to spin off the methanol and dry the carousel completes the clean cycle.

Equipment Priming

Before using the equipment, the equipment should be primed to fill the various reagent lines so that reagent spray takes place during the desired times and there is no lag time while lines and mixing chambers fill with reagent. To prime the lines, solenoid valve S-4 and S-3 are activated along with pumps 46 and 47 to produce the selected stain blend for the dilute stain step. Solenoids S-1 and S-2 are also activated during this period so that this concentrated staining solution passes through solenoid valves S-1 and S-2, mixing chambers MC-2 and MC-3, and nozzle 17. This fills line 54 with concentrated staining solution. Solenoid valve S-1 does not operate during this time to mix and dilute the stain with buffer. To prime line 50 leading to nozzle 16 and mixing chamber MC-1, solenoid valve S-4 is activated to produce the concentrated staining mixture. S-3 is activated during this period to route the concentrated staining mixture through line 50 and mixing chamber MC-1 to nozzle 16. During the same period, solenoid valve S-1 is deactivated and solenoid valves S-7 and S-2 are activated, along with pump 45, so that line 51 and mixing chambers MC-2 and MC-3 are filled with rinse buffer. A short high speed spin of the carousel completes the priming of the equipment.

An abbreviated "nozzle" clean cycle can be activated, such as by pressing a clean keypad on the control panel twice. This causes pump 48 and solenoid valve S-6 to activate. Methanol flows through check valve 55 in line 56 to nozzle 16. A six and one half pound check valve has been found satisfactory. During this operation, valve S-3 is in rest condition so that no flow from line 50 can take place. Thus, methanol will flow through nozzle 16 to clean it, but will not flow into mixing chamber MC-1 or line 50. This nozzle cleaning cycle provides a less expensive cleaning of the nozzle 16. The repriming of the nozzle 16 is the same as described above but only a short reprime is required.

Pump Pressures

It has been found that the equipment works well to carry out the process of the invention when pump 40 produces ten PSIG, and pumps 41, 42, and 43 produce nine PSIG. However, various other pressures could be used.

Reagents

The concentrated staining solution and the stain components making up the staining solution are important features of the invention. The concentrated staining solution contains between about 90% and 40% organic solvent, about 10% to about 60% water, and about 1 to about 5 g/L of thiazin and/or eosin dye. However, as indicated, combination thiazin-eosin stains are unstable in any solution with water so cannot be prepared and stored before use. They have to be prepared shortly before use. Water containing thiazin and eosin stains alone are stable and can be prepared ahead and then mixed in the staining equipment just prior to use. Thus, the invention uses a thiazin stain and an eosin stain that are mixed, as indicated above, to form the final concentrated staining solution that is applied to the samples on the slides. When reference is made in this application, including the claims, to a stain, staining solution, or stain for use in Romanowsky type staining, such reference or similar reference may refer to or include the separate thiazin or eosin stains or the stains or staining solutions formed by mixing and/or diluting such separate thiazin and eosin stains. In order to produce the desired mixed stain or staining solution, the thiazin stain contains between about 90% and about 40% organic solvent, between about 10% and about 60% water, and between about 1 and about 5 grams of thiazin dye. The thiazin dye will usually be a mixture of azure B and methylene blue, but could be either alone. It is presently preferred to use twice as much azure B as methylene blue. The organic solvent will usually be methanol. Various buffering components will also be included, such as imidazole, maleic acid, and KOH. Triton X-100 (polyoxyethylene (10)isooctylcyclohexyl ether) can be added to reduce precipitation. A preferred formulation of thiazin stain contains about 65% organic solvent, and about 35% water, with about 2 to about 4 g/L of thiazin dye and various buffering ingredients. Such stain will be adjusted to a pH of about 7. A specific preferred formulation is given in the example.

The eosin stain contains about 65% organic solvent, usually methanol, about 35% water, and between about 1 and about 4 g/L of eosin dye. It is not necessary to include buffering components in the eosin stain as such buffering components will come into the mixed stain from the thiazin stain, but can be included, if desired, or will be included if the eosin stain is used alone. Such stain will be adjusted to a pH of about 7. A specific preferred formulation is given in the example.

In mixing the staining solution, various proportions of the thiazin and eosin stains can be used. It is presently preferred to use about equal proportion of the two stains.

Various dilution buffers may be used, with a currently preferred formulation given in the example.

EXAMPLE

Equipment

Automated staining equipment as described above that is capable of mixing the thiazin and eosin stains in the desired proportion and diluting the resulting stain with the buffer employed is necessary for carrying out the process of the invention. An Aerospray® 7150 stainer sold by Wescor Inc., Logan, Utah, is suitable, and has been specifically programmed for carrying out the method of the invention. With such equipment, the rinse buffer is loaded into reservoir 40, the thiazin stain into reservoir 41, the eosin stain into reservoir 42, and the methanol into reservoir 43. An example of the method of the invention using the stains of the invention was conducted using a prototype Aerospray® 7150 as follows:

Stains

For the example, the thiazin and eosin stains had the following formulas:
1. Thiazin Stain
35% water
65% methanol
5.44 g/L Imidazole
9.28 g/L Maleic Acid
4.25 g/L KOH
2.29 g/L Azure B
1.15 g/L Methylene blue
10 g/L Triton X-100
Adjusted to pH 7.0
2. Eosin Stain
35% water
65% methanol
1.51 g/L Eosin
Adjusted to pH 7.0

Rinse Buffer

The rinse buffer had the following formula:
0.408 g/L Imidazole
0.696 g/L Maleic Acid
0.458 g/L KOH
0.05 g/L Triton X-100
Adjusted to pH 6.8

Process
  a. With the carousel rotating at 20 RPM, each slide was given two hits (six seconds of spray) of absolute methanol to fix the cells prior to staining. This was followed by a 30 second period of 20 RPM rotation (30 second wait time) to allow the slides to dry.
  b. The stainer was programmed to mix equal parts of the thiazin stain and the eosin stain to form the concentrated staining solution and to apply two hits (six seconds at 20 RPM) of the concentrated staining solution to each of the slides.
  c. The slides were spun at 600 RPM for 26 seconds.
  d. The slides were rinsed with rinse buffer. Each slide received three hits (nine seconds) followed by a one second high speed spin (600 RPM). This step was repeated once.
  e. The slides were stained with a dilute stain. The thiazin and eosin stains were blended in equal proportions and the resulting mixture was blended with five volumes of dilution buffer. Each slide received three hits (nine seconds) followed by a one second spin at 600 RPM. This was followed by three additional cycles of two hits of dilute stain (six seconds), a 30 second spin at 600 RPM, and a 30 second wait (30 second spin at 20 RPM).
  f. The slides were then rinsed with rinse buffer. Each slide received three hits (nine seconds) of rinse buffer. Slides then received a one second spin at 600 RPM. Four additional cycles of rinse buffer were applied.
  g. The slides were dried by centrifuging at 1,000 RPM for 30 seconds.

The specimens stained in the example showed excellent basophil granule preservation and good color corresponding to and easily readable as Romanowsky stained samples.

Whereas the invention is here illustrated and described with reference to embodiments thereof presently contemplated as the best mode of carrying out the invention in actual practice, it is to be understood that various changes may be made in adapting the invention to different embodiments without departing from the broader inventive concepts disclosed herein and comprehended by the claims that follow.

The invention claimed is:

1. A concentrated stain for Romanowsky type staining using automated staining equipment, comprising:
   about 40% to about 90% by volume organic solvent;
   about 60% to about 10% by volume water;
   about 1 to about 5 grams per liter of dye chosen from the group consisting of thiazin dye, eosin dye, or a mixture thereof; and
   said stain being buffered to a pH of from about 6 to about 9.

2. A concentrated stain for Romanowsky type staining according to claim 1, wherein the stain is a thiazin stain and the dye is a thiazin dye.

3. A concentrated stain for Romanowsky type staining according to claim 2, wherein the thiazin stain comprises about 35% water by volume, about 65% by volume organic solvent, and about 2 to about 4 g/L thiazin dye chosen from the group consisting of azure B, methylene blue, or a mixture thereof.

4. A concentrated stain for Romanowsky type staining according to claim 3, wherein the thiazin stain comprises about 35% by volume water, about 65% by volume organic solvent, about 2.29 g/L azure B, and about 1.15 g/L methylene blue, and is adjusted to a pH of about 7.0.

5. A concentrated stain for Romanowsky type staining according to claim 4, wherein the thiazin stain comprises about 35% by volume water, about 65% by volume organic solvent, about 5.44 g/L imidazole, about 9.28 g/L maleic acid, about 4.25 g/L KOH, about 2.29 g/L azure B, and about 1.15 g/L methylene blue, and is adjusted to a pH of about 7.0.

6. A concentrated stain for Romanowsky type staining according to claim 4, wherein the organic solvent is methanol.

7. A concentrated stain for Romanowsky type staining according to claim 1, wherein the stain is an eosin stain and the dye is an eosin dye.

8. A concentrated stain for Romanowsky type staining according to claim 7, wherein the eosin stain comprises about 35% by volume water, about 65% by volume organic solvent, and about 1.51 g/L eosin, and is adjusted to a pH of about 7.0.

9. A concentrated stain for Romanowsky type staining according to claim 8, wherein the organic solvent is methanol.

10. A concentrated stain for Romanowsky type staining according to claim 1, wherein the stain is a mixture of a thiazin stain comprising about 35% by volume water, about 65% by volume organic solvent, and about 2 to about 4 g/L thiazin dye chosen from the group consisting of azure B, and methylene blue, or a mixture thereof, adjusted to a pH of about 7.0; and an eosin stain comprising about 35% by volume water, about 65% by volume organic solvent, and about 1 to about 4 g/L eosin, adjusted to a pH of about 7.0.

11. A concentrated stain for Romanowsky type staining according to claim 10, wherein the thiazin stain comprises about 35% by volume water, about 65% by volume organic solvent, about 2.29 g/L azure B, and about 1.15 g/L methylene blue, and is adjusted to a pH of about 7.0.

12. A concentrated stain for Romanowsky type staining according to claim 11, wherein the thiazin stain comprises about 35% by volume water, about 65% by volume organic solvent, about 5.44 g/L imidazole, about 9.28 g/L maleic acid, about 4.25 g/L KOH, about 2.29 g/L azure B, and about 1.15 g/L methylene blue, and is adjusted to a pH of about 7.0.

13. A concentrated stain for Romanowsky type staining according to claim 10, wherein the eosin stain contains about 1.51 g/L eosin.

14. A concentrated stain for Romanowsky type staining according to claim 10, wherein the organic solvent is methanol.

15. A concentrated stain for Romanowsky type staining according to claim 10, wherein the stain is a mixture of about equal parts of the thiazin stain and the eosin stain.

16. A concentrated stain for Romanowsky type staining according to claim 10, wherein the stain is diluted from between about 1:2 and about 1:15 with a dilution buffer to form a dilute stain.

17. A concentrated stain for Romanowsky type staining according to claim 10, wherein the stain is diluted from between about 1:2 and about 1:15 with a dilution buffer to form a dilute stain, and wherein the dilution buffer comprises about 0.408 g/L imidazole, about 0.696 g/L maleic acid, about 0.458 g/L KOH, and about 0.05 g/L polyoxyethylene(10)isooctylcyclohexyl ether, and the solution is adjusted to a pH of between about 6.8 and about 7.2.

* * * * *